US012644865B2

(12) United States Patent
Sai

(10) Patent No.: US 12,644,865 B2
(45) Date of Patent: Jun. 2, 2026

(54) NON-INVASIVE ADVANCED SENSORY SYSTEM FOR REAL-TIME MONITORING AND DIAGNOSIS OF ELECTROLYZERS, ELECTROLYTES AND A LITHIUM-ION BATTERY (LIB)

(71) Applicant: Honeywell International Inc., Charlotte, NC (US)

(72) Inventor: Bin Sai, The Hague (NL)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 318 days.

(21) Appl. No.: 18/425,391

(22) Filed: Jan. 29, 2024

(65) Prior Publication Data

US 2025/0244293 A1     Jul. 31, 2025

(51) Int. Cl.
*G01N 29/04* (2006.01)
*C25B 15/00* (2006.01)
(Continued)

(52) U.S. Cl.
CPC ........... *G01N 29/043* (2013.01); *C25B 15/00* (2013.01); *G01B 7/16* (2013.01); *G01N 33/0027* (2013.01);
(Continued)

(58) Field of Classification Search
CPC ... G01N 2291/02836; G01N 2291/044; G01N 29/043; G01N 2291/0289;
(Continued)

(56) References Cited

U.S. PATENT DOCUMENTS 8,129,998 B2    3/2012  Watanabe et al.
8,541,122 B2    9/2013  Fulop et al.
(Continued)

FOREIGN PATENT DOCUMENTS

CN         116297662 A       6/2023
DE     102024113033 A1 *    6/2025    ............. G01S 15/86
(Continued)

OTHER PUBLICATIONS

European Patent Application No. EP 4 607 188 A3, Partial European Search Report.
(Continued)

*Primary Examiner* — Andre J Allen
(74) *Attorney, Agent, or Firm* — Ingrassia Fisher & Lorenz LLP

(57)     ABSTRACT

A non-intrusive sensing system for monitoring an electrochemical device and a method of operating the non-intrusive sensing system can include multi-static ultrasonic sensors for detecting data indicative of a property of electrolytic media in an electrochemical device, an acoustic sensor for detecting and measuring a signature of electrodes associated with a health condition of the electrochemical device. A temperature sensor can be used to detect surface temperature data and correlate the surface temperature data with the signature identified and extracted by the acoustic sensor and the data indicative of the property of the electrolytic media. The data detected by the multi-static ultrasonic sensors, the signature detected by the acoustic sensor, and the surface temperature data identified can be subject to feature extraction and processing by a detection and prediction model to produce information pertaining to the safety, reliability and operating efficiency of the electrochemical device.

20 Claims, 9 Drawing Sheets

(51) Int. Cl.

| | |
|---|---|
| *G01B 7/16* | (2006.01) |
| *G01N 33/00* | (2006.01) |
| *H01M 10/48* | (2006.01) |

(52) U.S. Cl.
CPC ...... *H01M 10/48* (2013.01); *G01N 2291/023* (2013.01); *G01N 2291/0289* (2013.01)

(58) Field of Classification Search
CPC ......... G01N 2291/2694; G01N 29/041; G01N 29/07; G01N 29/222; G01N 2291/0251; G01N 2291/02854; G01N 2291/0421; G01N 2291/0427; G01N 29/223; G01N 29/2418; G01N 29/4436; G01N 29/46; G01N 2291/015; G01N 2291/02845; G01N 2291/0423; G01N 2291/0426; G01N 2291/045; G01N 2291/048; G01N 2291/102; G01N 2291/105; G01N 29/02; G01N 29/024; G01N 29/245; G01N 29/28; G01N 29/4427; G01N 2203/0244; G01N 2203/0658; G01N 2203/0682; G01N 2291/011; G01N 2291/0234; G01N 2291/02433; G01N 2291/0258; G01N 2291/0422; G01N 2291/056; G01N 2291/101; G01N 2291/103; G01N 29/032; G01N 29/069; G01N 29/22; G01N 29/225; G01N 29/227; G01N 29/228; G01N 29/2437; G01N 29/2462; G01N 29/262; G01N 29/265; G01N 29/348; G01N 29/38; G01N 29/4409; G01N 29/4481; H01M 10/48; H01M 10/484; H01M 10/486; G01B 7/16
See application file for complete search history.

(56) References Cited

U.S. PATENT DOCUMENTS

| | | | |
|---|---|---|---|
| 9,008,744 B2 | 4/2015 | Rose et al. | |
| 9,583,796 B2 | 2/2017 | Saha et al. | |
| 10,344,386 B2 | 7/2019 | Kodama et al. | |
| 10,613,567 B2 | 4/2020 | Rooyakkers et al. | |
| 10,667,754 B2 | 6/2020 | Starr et al. | |
| 11,193,979 B2 * | 12/2021 | Steingart ........... | G01N 29/4418 |
| 11,527,783 B2 * | 12/2022 | Ladpli ............... | G01N 29/4436 |
| 2019/0117083 A1 | 4/2019 | Wang et al. | |
| 2022/0088636 A1 | 3/2022 | Chen et al. | |
| 2024/0337034 A1 * | 10/2024 | Zheng .................... | C25B 15/06 |
| 2025/0362352 A1 * | 11/2025 | Zheng ................. | G01R 31/367 |

FOREIGN PATENT DOCUMENTS

| | | | | |
|---|---|---|---|---|
| WO | WO-2015023820 A2 * | 2/2015 | ........... | H01M 10/48 |
| WO | WO-2021113879 A2 * | 6/2021 | ......... | H01M 10/484 |

OTHER PUBLICATIONS

Wang Zuolu et al, "A review on rapid state of health estimation of lithium-ion batteries in electric vehicles", Sustainable Energy Technologies and Assessments, vol. 60, Dec. 1, 2023 (Dec. 1, 2023), p. 103457, XP093261868, NL ISSN: 22313-1388, DOI: 10.1016/j.seta.2023.103457.

Wang Zuolu et al, "Active acoustic emission sensing for fast co-estimation of state of charge and state of health of the lithium-ion battery," Journal of Energy Storage, Elsevier BV, NL, vol. 64, Mar. 23, 2023.

* cited by examiner

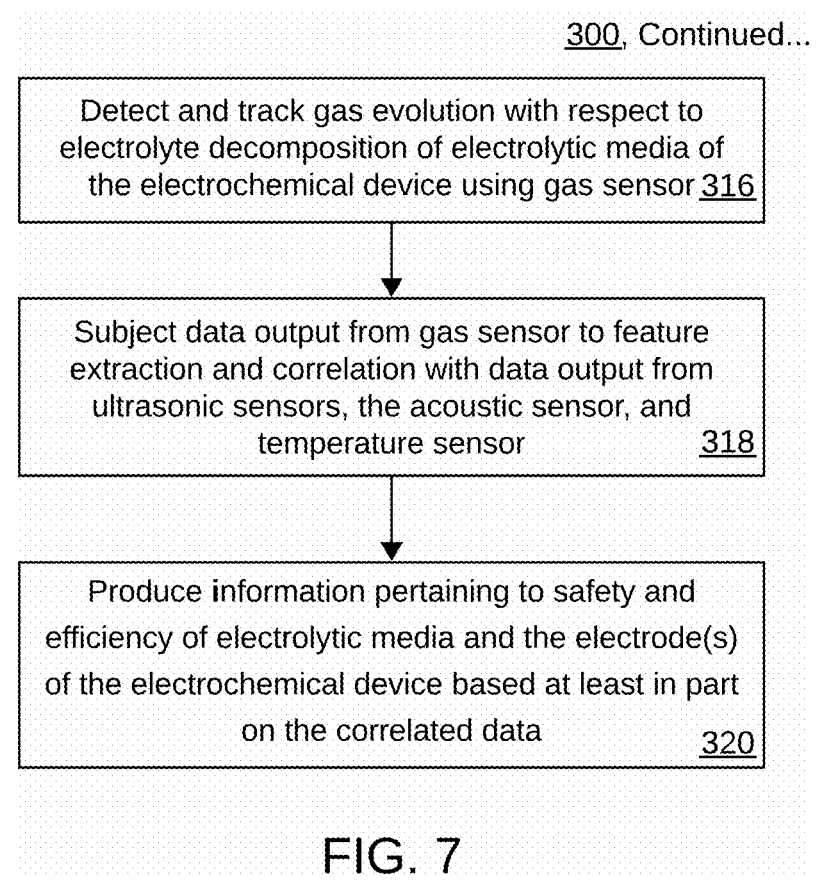

300, Continued...

Detect and track gas evolution with respect to electrolyte decomposition of electrolytic media of the electrochemical device using gas sensor 316

Subject data output from gas sensor to feature extraction and correlation with data output from ultrasonic sensors, the acoustic sensor, and temperature sensor    318

Produce information pertaining to safety and efficiency of electrolytic media and the electrode(s) of the electrochemical device based at least in part on the correlated data    320

FIG. 7

NON-INVASIVE ADVANCED SENSORY SYSTEM FOR REAL-TIME MONITORING AND DIAGNOSIS OF ELECTROLYZERS, ELECTROLYTES AND A LITHIUM-ION BATTERY (LIB)

TECHNICAL FIELD

Embodiments are generally related to the fields of energy storage, renewable energy, and electrochemical systems. Embodiments further relate to sensor technologies and monitoring systems and methods. Embodiments also relate to the monitoring and diagnosing of electrochemical reactions in electrolyzers and batteries.

BACKGROUND

In response to the urgent global need for carbon neutrality and sustainability in the coming decades to combat climate change, a paradigm shift in the world's energy landscape is needed, which will involve transitioning from fossil fuels to green energy sources. Electrolytes and electrolyzers can play a pivotal role in this macro trend, contributing significantly to electrification, green energy generation, and electrochemical energy storage and energy conversion systems.

Current challenges, however, include the lack of real-time monitoring and diagnosis capabilities at the device inside level, specifically addressing issues such as electrochemical reactions, electrode swelling, fracturing, metal dissolution, electrolyte ageing and decomposition, status of charge, contaminated electrodes, degradation of membrane electrode assembly, shuttling of reduction-oxidation contaminants, and unexpected increases in electrolyte interphase, etc., which collectively can contribute to safety, efficiency and performance degradation in electrolyzers and batteries.

To address these challenges, a novel sensing approach is required, which aims to enhance the monitoring and diagnosis of electrolyzers and batteries. Traditional methods have primarily focused on measuring voltage and current and temperature as fundamental data collection techniques. These methods, however, lack detailed insights into crucial aspects such as electrochemical reactions, electrolyte aging, state of charge, drying or wetting of electrodes, and the presence of gases within electrodes, offering limited information about the overall health condition of the system in real time. Detecting the thermal runways, for example, is often too late which can lead to unexpected disastrous hazards. Therefore, a new non-invasive sensory system for monitoring and diagnosis is needed, which can detect the real-time conditions of internal electrolyzers and electrolytes and batteries to enhance safety and preventive maintenance and efficient operations.

An ongoing need exists for a solution involving advanced monitoring and diagnosis approaches that can provide comprehensive insights into the safety, reliability, and lifetime of electrolyzers and batteries. This solution should go beyond conventional approaches by integrating advanced sensing technologies that can enable real-time assessment of key parameters critical for maintaining optimal performance and safety in the context of the global transition to green energy.

BRIEF SUMMARY

The following summary is provided to facilitate an understanding of some of the features of the disclosed embodiments and is not intended to be a full description. A full appreciation of the various aspects of the embodiments disclosed herein can be gained by taking the specification, claims, drawings, and abstract as a whole.

It is, therefore, one aspect of the embodiments to provide for an improved sensing system for monitoring the health of an electrochemical device such as a lithium ion battery (LIB). The electrochemical device can refer to cell level, stack level and module level.

It is another aspect of the embodiments to provide for the monitoring and diagnosing of electrochemical reactions in electrochemical devices including electrolyzers and fuel cell batteries. The electrochemical devices can refer to cell level, stack level and module level.

It is a further aspect of the embodiments to provide for an intelligent sensing system that integrates special ultrasonic transducers, wideband acoustic sensor, gas and temperature sensors for non-invasive monitoring of internal electrochemical reaction processes within an electrochemical device.

It is also an aspect of the embodiments to provide for a non-invasive advanced sensory system for real-time monitoring and diagnosis of electrochemical devices with a focus on assessing electrolyzers, electrolytes, and lithium-ion batteries.

The aforementioned aspects and other objectives can now be achieved as described herein. In an embodiment, a non-intrusive sensing system for monitoring an electrochemical device, can include: multi-static ultrasonic sensors for detecting data indicative of a property of electrolytic media in an electrochemical device; an acoustic sensor for detecting and measuring a signature of at least one electrode associated with a health condition of the electrochemical device; and a temperature sensor for detecting surface temperature data associated with the electrochemical data and correlating the surface temperature data with the signature identified and extracted by the acoustic sensor and the data indicative of the property of the electrolytic media detected by the multi-static ultrasonic sensors. The data detected by the multi-static ultrasonic sensors, the signature detected by the acoustic sensor, and the surface temperature data identified by the temperature sensor can be subject to feature extraction and processing by a detection and prediction model to produce information pertaining to safety and operating efficiency of the electrochemical device.

In an embodiment of the non-intrusive sensing system, the sensor data derived from the multi-static ultrasonic sensors, the acoustic sensor, and the temperature sensor can be fused based on multiple sensor inputs from the multi-static ultrasonic sensors and the acoustic sensor to form a uniform feature vector space for faulty detection and identification and prediction.

In an embodiment of the non-intrusive sensing system, the health condition of the electrochemical device can include data indicative of a fracture or cracks of electrodes.

In an embodiment of the non-intrusive sensing system, a gas sensor can be implemented for detecting and tracking a gas evolution and possible venting with respect to electrolyte decomposition of the electrolytic media of the electrochemical device, wherein data output from the gas sensor is subject to the feature extraction and correlation with data output from the ultrasonic sensor, the acoustic sensor and temperature sensor for use in producing and validating the early-sign information pertaining to the safety and the efficiency of the electrolytic media and the at least one electrode of the electrochemical device. The validation using gas sensor is necessary to correlate the gas event evolution with ultrasonic and acoustic signal signatures without getting the electrochemical device into full malfunction situation during the feature data training phase.

In an embodiment of the non-intrusive sensing system, the electrochemical device can be a device under test (DUT).

In an embodiment of the non-intrusive sensing system, the ultrasonic sensor can be located on the electrochemical device and can transmit a pulse amplitude and/or multi-frequency-modulated ultrasonic signal through the electrolytic media. The pulse-modulated ultrasonic signal can include data indicative of a property of the electrolytic media, wherein the property of the electrolytic media is usable for a construction of chemical-physical thermal metrics during a cycle, and the data can determine a health status of reduction-oxidation or charge and discharge cycles of the electrochemical device.

In an embodiment of the non-intrusive sensing system, the acoustic sensor can be a wideband acoustic sensor with, for example, at least 20 KHz bandwidth, wherein the wideband acoustic sensor is located on the electrochemical device and the signature of the at least one electrode associated with the electrochemical device allows the acoustic sensor to measure an electrode fracture and phase transitions of the at least one electrode during an operation of the electrochemical device.

In an embodiment of the non-intrusive sensing system, the acoustic sensor can be a MEMS or non-MEMS wideband free-field based sensor and pressure-field based sensor elements or microphones in which the microphones can form a part of a DUT wall and can measure sound pressure on the wall of DUT.

In an embodiment of the non-intrusive sensing system, the microphones can include a free-field microphone that can measure the sound pressure where a sensor front-end is located.

In an embodiment of the non-intrusive sensing system, the acoustic sensor can include at least two types of acoustic sensors that can work together to eliminate background noise and extraneous disturbances to determine correct signals emanating from within the electrochemical device.

In an embodiment of the non-intrusive sensing system, the temperature sensor may be a surface temperature sensor that can be configured to track a temperature correlation with acoustic and ultrasonic sensory data respectively output from the acoustic sensor and the ultrasonic sensor, which together can facilitate a development of an internal thermo-dynamic model with respect to the electrochemical device for safety and efficiency prediction.

In an embodiment of the non-intrusive sensing system, a piezoelectric strain sensor can be implemented, which can verify expansion and contraction data and can correlate the expansion and contraction data with ultrasonic signal signatures derived from the multi-static ultrasonic sensors.

In an embodiment of the non-intrusive sensing system, the piezoelectric strain sensor can detect pressure waves impinging on an inner wall of the electrochemical device or DUT.

In an embodiment of the non-intrusive sensing system, the piezoelectric strain sensor may be an accelerometer or another type of strain sensor.

In an embodiment of the non-intrusive sensing system, the acoustic sensor can include a signal processor that can extract the signature of the at least one electrode attributed to one or more of, for example, electrochemical reaction grinding, gassing, and expansion and contraction.

In an embodiment, a non-intrusive sensing system for monitoring an electrochemical device, can include: a plurality of ultrasonic sensors for detecting data indicative of a property of electrolytic media in an electrochemical device; an acoustic sensor for detecting and measuring a signature of at least one electrode associated with a health condition of the electrochemical device; a strain sensor that verifies expansion and contraction data and correlates the expansion and contraction data with ultrasonic signal signatures derived from the plurality of ultrasonic sensors, wherein the strain sensor further detects pressure changes within a wall of the electrochemical device; and a temperature sensor for detecting surface temperature and temperature change data associated with the electrochemical data and correlating the surface temperature data with the signature identified and extracted by the acoustic sensors and the data indicative of the property of the electrolytic media detected by the plurality of ultrasonic sensors, wherein the data detected by the plurality of ultrasonic sensors, the signature detected by the acoustic sensor, and the surface temperature data identified by the temperature sensor are subject to feature extraction and processing by a detection and prediction model to produce information pertaining to safety and operating efficiency of the electrochemical device.

In an embodiment, a method of operating a non-intrusive sensing system that monitors an electrochemical device, can involve: detecting with multi-static ultrasonic sensors, data indicative of a property of electrolytic media in an electrochemical device using multi-static ultrasonic sensors configured for detecting the data indicative of the property of the electrolytic media in the electrochemical device; detecting and measuring with an acoustic sensor, a signature of at least one electrode associated with a health condition of the electrochemical device; detecting with a temperature sensor, surface temperature data associated with the electrochemical data and correlating the surface temperature data with the signature identified and extracted by the acoustic sensor and the data indicative of the property of the electrolytic media detected by the multi-static ultrasonic sensors; and subjecting the data detected by the multi-static ultrasonic sensors, the signature detected by the acoustic sensors, and the surface temperature data identified by the temperature sensor to feature extraction and processing by a detection and prediction model for the generation of information pertaining to safety and operating efficiency of the electrochemical device.

An embodiment of the method can further involve fusing sensor data derived from the multi-static ultrasonic sensors, the acoustic sensors, and the temperature sensor based on multiple sensor inputs from the multi-static ultrasonic sensors and the acoustic sensors to form a uniform feature vector space for faulty detection, classification and identification and prediction.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1B (left) illustrates an alternative view of an electrochemical device with a shape similar to that of the electrochemical device shown in FIG. 1A, in accordance with yet another embodiment;

FIG. 7 illustrates additional and optional operational steps of the method monitoring an electrochemical device, which can be implemented in accordance with an embodiment;

In the drawings described and illustrated herein, identical or similar parts and elements are generally indicated by identical reference numerals.

DETAILED DESCRIPTION

Figures 1A, 1B:
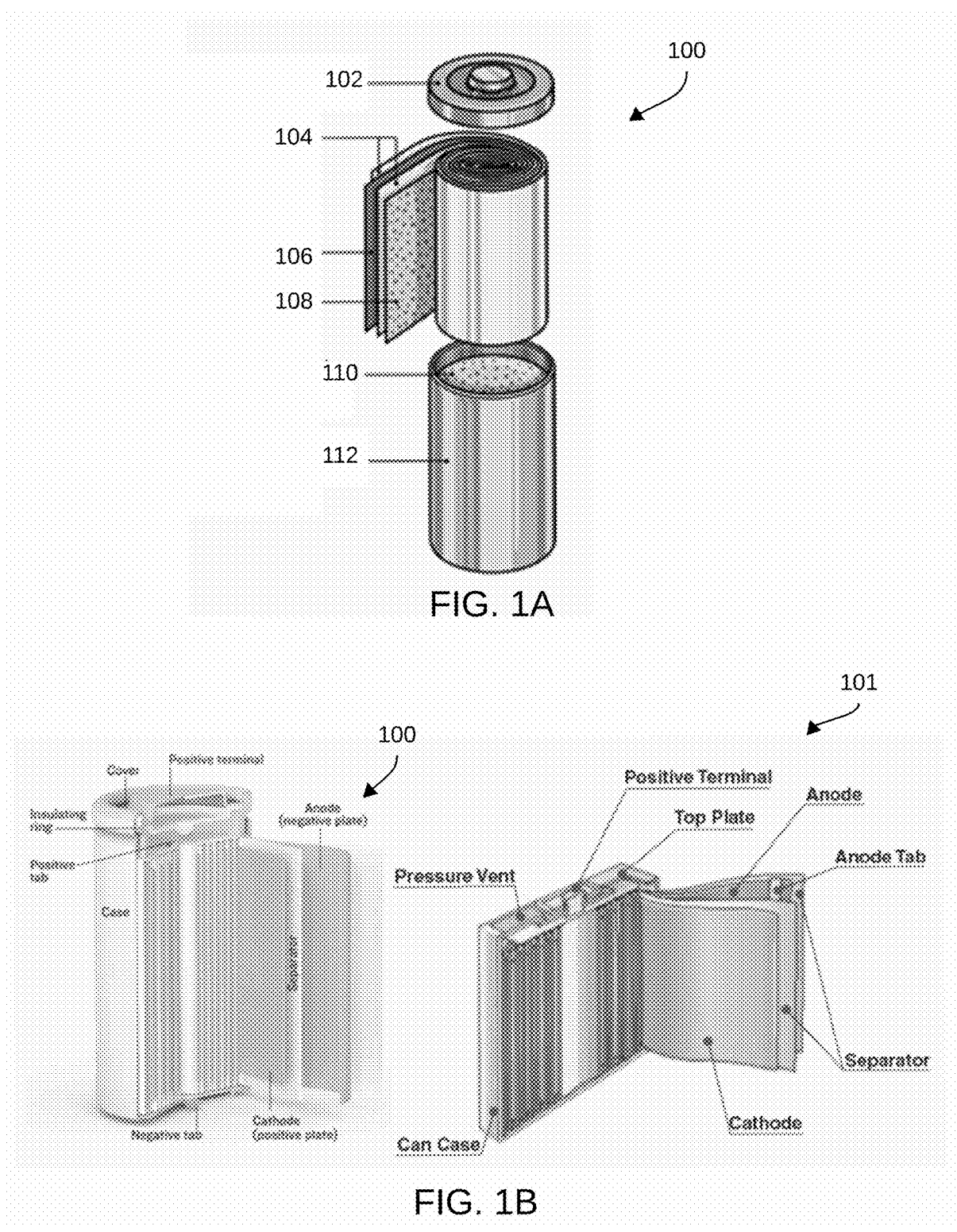
FIG. 1A illustrates a cut-away view of a shape of an electrochemical device, in accordance with an embodiment.
FIG. 1B (right) illustrates a prismatic shape of an electrochemical device, in accordance with another embodiment.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other issues, subject matter may be embodied as methods, devices, components, or systems. Accordingly, embodiments may, for example, take the form of hardware, software, firmware, or a combination thereof. The following detailed description is, therefore, not intended to be interpreted in a limiting sense.

Throughout the specification and claims, terms may have nuanced meanings suggested or implied in context beyond an explicitly stated meaning. Likewise, phrases such as "in one embodiment" or "in an example embodiment" and variations thereof as utilized herein may not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part.

In general, terminology may be understood, at least in part, from usage in context. For example, terms such as "and," "or," or "and/or" as used herein may include a variety of meanings that may depend, at least in part, upon the context in which such terms are used. Generally, "or" if used to associate a list, such as A, B, or C, is intended to mean A, B, and C, here used in the inclusive sense, as well as A, B, or C, here used in the exclusive sense. In addition, the terms "one or more" or "at least one" as used herein, depending at least in part upon context, may be used to describe any feature, structure, or characteristic in a singular sense or may be used to describe combinations of features, structures, or characteristics in a plural sense. Similarly, terms such as "a," "an," or "the", again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context. Furthermore, the term "at least one" as utilized herein can refer to "one or more". For example, "at least one widget" may refer to "one or more widgets".

As will be discussed in greater detail below by way of references to the various figures provided herein as a part of this detailed description, embodiments relate to improved monitoring and sensing devices, methods, and systems in the field of energy storage, renewable energy, and electrochemical systems. The embodiments offer solutions that can address challenges and solutions related to the safety, reliability, and lifetime of batteries. These embodiments can facilitate the transition from fossil fuels to green energy through a unique and novel approach to monitoring and diagnosing electrochemical reactions in electrochemical systems including electrolyzers and batteries.

Note that the term electrolyzer as utilized herein can relate to a device that can employ electrolysis, a process in which electrical energy can be used to drive a non-spontaneous chemical reaction. There are several types of electrolyzer technologies, which can be utilized to implement an electrolyzer, including proton exchange membrane (PEM), alkaline, anion exchange membrane (AEM), and solid oxide technologies. Currently PEM water electrolysis is an environmentally friendly method in which an electrolyzer can facilitate the decomposition of pure water (H2O) into its constituent elements, hydrogen (H2) and oxygen (O2), through the electrolytic process by applying an electric current.

The basic setup of an electrolyzer can include electrodes (an anode and a cathode) immersed in an electrolyte solution. When an electric current is applied, water molecules are split into hydrogen and oxygen ions. Hydrogen gas is generated at the cathode, while oxygen gas is produced at the anode. Electrolyzers play a significant role in the production of hydrogen for various applications, including clean energy storage and fuel cell technologies. They contribute to the development of sustainable energy systems by providing a means to produce hydrogen gas without the emission of greenhouse gases, as opposed to traditional methods of hydrogen production.

FIG. 1A illustrates a cut-away view of an electrochemical device 100, in accordance with an embodiment. The electrochemical device 100 can include a casing 112, which is shown as generally prismatic or cylindrical or tubular in shape in FIG. 1A. An electrolytic solution 110 (e.g., electrolytic media) can be contained within and located in the casing 112. An anode 106 and a cathode 108 along with one or more separators 104 can be contained within the casing 112 and enclosed by a cap 102. In some embodiments, the electrochemical device 100 may be or may form a part of a lithium-ion battery (LIB) stack and/or system and can be implemented in the context of an LIB pack module.

It can be appreciated that the electrochemical device 100 in some embodiments may be a device under test (DUT) which can relate to a specific device or system that is being tested or evaluated in the context of a measurement. The term DUT is commonly used in various fields, including electronics, telecommunications, engineering, and research. Another term for DUT is a "test subject" or a "test specimen," which can encompass a wider range of objects or systems that may undergo testing, evaluation, or experimentation in various industrial, scientific and technical domains. The choice of terminology may depend on the specific context and industry in which the testing may take place.

FIG. 1B illustrates pictorial views of the electrochemical device 100 and a prismatic shape view of an alternative electrochemical device 101, in accordance with another embodiment. The cylindrically-shaped electrochemical device 100 is shown at the left side of FIG. 1B and the prismatic electrochemical device 101 is shown on the right side of FIG. 1B. The configurations shown in FIG. 1B are provided herein to demonstrate alternative electrochemical device embodiments. For example, the electrochemical device 101 may be implemented as an electrolyzer, which can include components such as a cathode, an anode and a separator in addition to an anode tab. In addition, a can case as depicted in FIG. 1B can include a pressure vent and a top plate in addition to a positive terminal.

Figure 2:
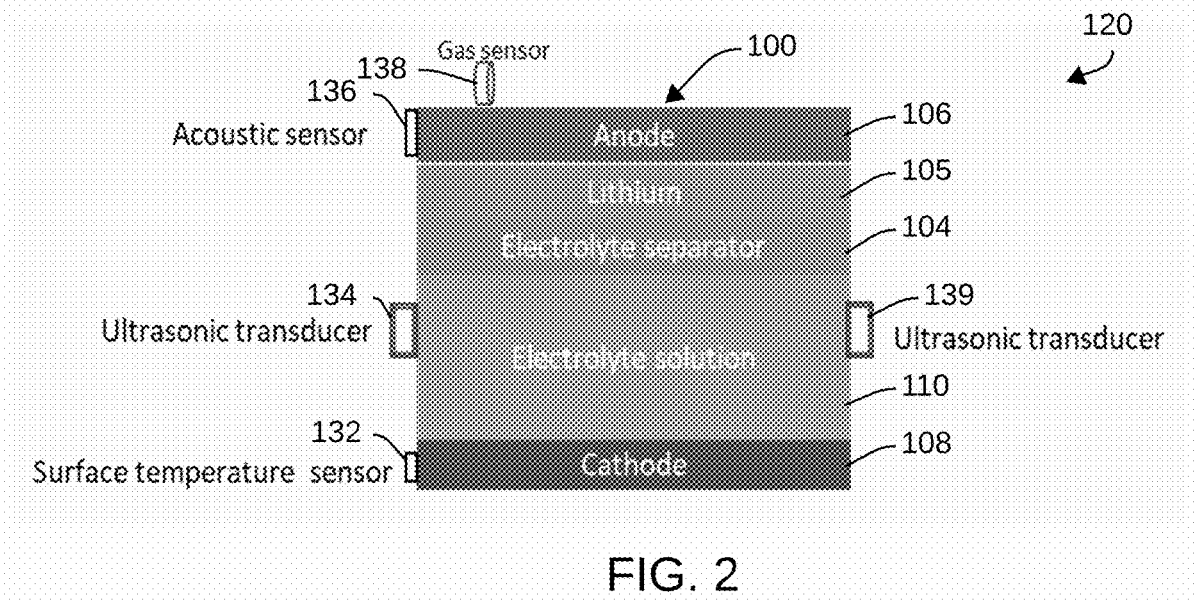
FIG. 2 illustrates a schematic diagram of a non-intrusive sensor array that can be located on the electrochemical device shown in FIG. 1, in accordance with an embodiment.

FIG. 2 illustrates an example of a sensor array 120, which can be implemented in accordance with an embodiment. The example sensor array 120 shown in FIG. 2 can include a number of sensors such as, for example, a surface temperature sensor 132, an ultrasonic transducer 134, an acoustic sensor 136, a gas sensor 138, an ultrasonic transducer 139 and/or other types of sensors. The sensor array 120 can functions as a non-intrusive sensor array as discussed in greater detail herein. This sensor array 120 can be located on the electrochemical device 100 and function as a sensor array of ultrasonic transducers and acoustic sensors and/or other types of sensor to measure, for example, an LIB pack module.

The electrochemical device 100 can thus include the sensor array 120 including the acoustic sensor 136 and other sensors located on the electrochemical device 100. In the example embodiment shown in FIG. 2, the acoustic sensor 136 of the sensor array 120 can be positioned toward the upper left side of the acoustic sensor 136 with respect to the anode 106 or can be placed in other positions depending on the stack configuration and installation practice. A layer of lithium 105 can be located adjacent the anode 106 and an electrolytic separator 104. An electrolyte solution (e.g., electrolytic media) can be located between the electrolyte separator 104 and the cathode 108. Note that the acoustic sensing in this embodiment can relate to signal frequencies up to, for example, 20 KHz, which is distinctive from ultrasound frequencies that can be used in the range from 20 KHz onwards.

The ultrasonic sensor 139 (e.g., ultrasonic transducer with the frequency higher than 20 KHz, typically several hundreds of KHz) and the ultrasonic sensor 134 can be located on the electrochemical device 100 with respect to the electrolyte solution 110. The temperature sensor 132 (e.g., surface temperature sensor 132) can be located on the electrochemical device 100 with respect to the electrolyte solution 110 or near the cathode 108. In some embodiments, the gas sensor 138 may be located on the electrochemical device 100 near anode 106 or cathode 108 (which is not shown) or in a pressure vent position if available such as shown in FIG. 1B (right side of FIG. 1B), depending on the gas sensor type and DUT type. The sensor array 120 associated with the electrochemical device 100 may include two or more ultrasonic sensors such as the ultrasonic sensor 139 and the ultrasonic sensor 134 which can be configured to function with transit-measurements and reflecting-measurements (i.e., multi-static measurement modes).

Figure 3:
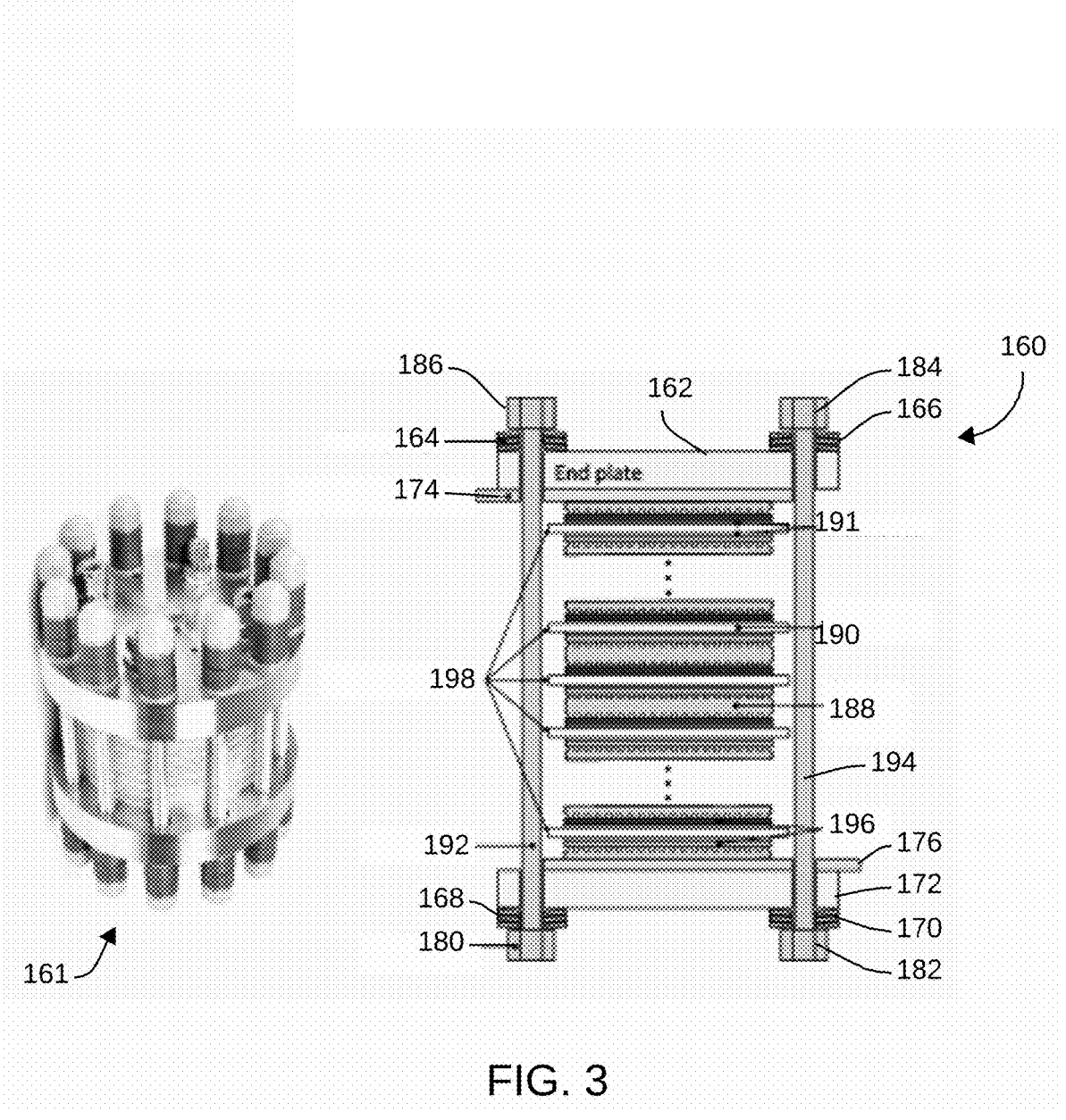
FIG. 3 illustrates a diagram of a multi-stack electrolyzer, which can be implemented in accordance with an embodiment.

FIG. 3 illustrates an exemplary schematic diagram of the internal structure of an electrolyzer 161, in accordance with an embodiment. That is, the electrolyzer 161 is shown at the left side of FIG. 3 and a cut-away view 160 of the electrolyzer 161 is shown at the right side of FIG. 3. The electrolyzer 161 can be implemented as a multi-stack electrolyzer in some embodiments. Note that in FIG. 3, the cut-away view 160 of the electrolyzer 161 is not actually a sensing system but represents the internal structure of the electrolyzer 161 depicted at the left side of FIG. 3.

The cut-away view 160 of the electrolyzer 161 depicts a number of components including, for example, an end plate 162 and an end plate 172, along with a group of springs such as flat springs 164, 165, 168, and 170 and a group of nuts 180, 182 184, and 186. The cut-away view 160 of the electrolyzer 161 also depicts a bolt 192 and a bolt 194. Additionally, a current collector 176 can be located above the end plate 172.

Furthermore, a current collector 174 can be located below the end plate 164. Individual cells 198 are shown in FIG. 3 as located generally between the end plates 162 and 172. In addition, one or more bipolar plates such as bipolar plate 188 are depicted in the cut-away view 160 of the electrolyzer 161, along with one or membranes such as membrane 190 and one or more electrodes such as electrodes 191. The cut-away view 160 of the electrolyzer 161 also depicts one or more porous transport layers (PTLs) 196.

Note that a PTL, or Porous Transport Layer, is a component commonly used in various electrochemical devices, such as, water electrolysis, fuel cells and batteries. The primary function of a PTL is to facilitate the transport of reactants, products, and ions within the electrochemical cell. It can serve as a porous medium that can allow gases or liquids to flow through, promoting efficient mass transport and electrochemical reactions.

In the context of a non-invasive real-time sensing system such as the sensing system 120 in FIG. 2, the system 120 can be applied to the electrolyzer 161 (and the cut-away view 160 of the electrolyzer 161) shown in FIG. 3. The PTL 196 can be incorporated in electrolyzer 161, for example, to enhance the movement of substances within the electrolyzer 161. Its porous nature can enable the efficient transport of relevant materials, contributing to the overall functionality and performance of the electrochemical processes occurring in the electrolyzer 161. Note in some embodiments, that the electrolyzer 161 can be used to generate hydrogen by applying proper electric voltage and current to it. It should be appreciated that the sensing system 120 shown in FIG. 2 is depicted with acoustic sensors, ultrasonic transducers and so on, in order to demonstrate a pictorial view of a working 'real world' sensing system. However, examples of such sensors are shown and described elsewhere herein such as in the configurations shown in FIG. 4A and FIG. 4B and other figures.

Figure 4A:
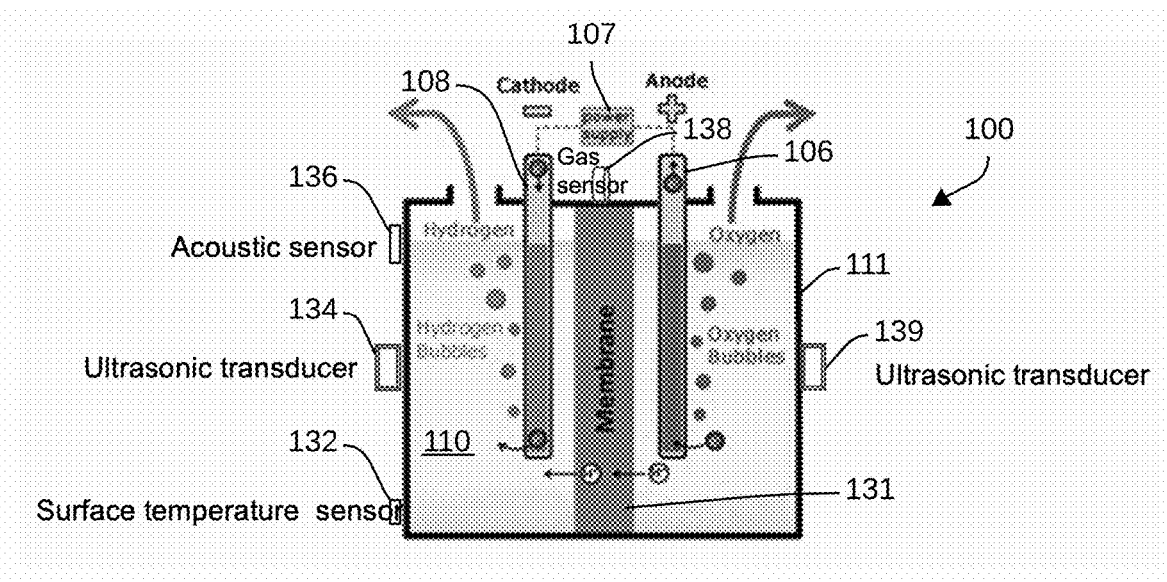
FIG. 4A illustrates a schematic diagram of a non-invasive real-time sensing array system located on the electrochemical device shown in FIG. 3, in accordance with an embodiment.

FIG. 4A illustrates a schematic diagram of the electrochemical device 100 (e.g., an electrolyzer) which can be implemented, in accordance with an embodiment. The electrochemical device 100 shown in FIG. 4A can include the acoustic sensor 136 and the temperature sensor 132. The acoustic sensor 136 and the temperature sensor 132 are located on the electrochemical device 100 along with ultrasonic sensor 134 and ultrasonic sensor 139. The electrochemical device 100 includes electrodes including cathode 108 and anode 106, along with gas sensor 138. A membrane 131 can be located in the electrolytic solution 110 within a container 111, which is analogous or similar to the casing 112 shown in FIG. 1A or the can case depicted in FIG. 1B. Hydrogen bubbles and oxygen bubbles are shown in FIG. 4 as a part of the electrochemical reaction facilitated by the electrochemical device 100. Note that the electrochemical device 100 can be implemented as a hermetically sealed electrochemical device.

Note that in some embodiments, each of the ultrasonic sensors 134 and ultrasonic sensor 139 can be implemented in the context of a multi-static configuration with forward (FWD) and backward (BWD) scattering measurements. A wideband acoustic sensor (e.g., with at least 20 KHz bandwidth) can be located on the electrochemical device 100 and the signature of one or more electrode associated with the electrochemical device 100 can allow the acoustic sensor to measure an electrode fracture and phase transitions of the electrodes during an operation of the electrochemical device 100.

As noted above, the example electrochemical device 100 shown in FIG. 4A can function as an electrolyzer in this particular embodiment. This electrochemical device 100 can incorporate several sensors and features to monitor and optimize its performance. The electrochemical device 100, as shown in the illustration of FIG. 4A, can be equipped with the acoustic sensor 136 and the temperature sensor 132. These sensors can be strategically positioned on the electrochemical device 100 to capture relevant data during its operation. Additionally, one or more ultrasonic sensors 134 and 139 are also present, contributing to a comprehensive sensing configuration in multi-static modes (e.g., in a configuration with one transmitter, two receivers on both sides of the electrochemical device 100 as transit and reflection measurements).

Key components within the electrochemical device 100 can include electrodes, specifically the cathode 108 and the anode 106. These electrodes can play a central role in the electrochemical reactions occurring within the device. The gas sensor 138 can be implemented as a supplementary element, which can be used for verification and can be responsible for detecting and monitoring gases leaks during the electrochemical processes where faulty effects may arise. Since the internal arrangement of the hermetically sealed electrochemical device 100 is invisible from outside the device, the voltage and the current meter, surface temperature and gas sensors, and even strain sensors may be implemented for verification and data training purposes but may not be required to function as primary sensors such as multi-static ultrasonic transducers and wideband acoustic sensors once the verification and training of the signal identification has been accomplished.

The electrolytic solution 110, situated within the container 111 can encompass the membrane 131, which can be strategically placed to facilitate the electrochemical reactions within the solution 110. The membrane 131 can serve as a separator, allowing selective transport of ions while preventing the mixing of different reactants, for example avoiding or reducing oxygen flowing to hydrogen chamber, or vice versa.

To better illustrate the electrochemical processes facilitated by the electrochemical device 100, FIG. 4A illustrates the formation of hydrogen bubbles and oxygen bubbles. This showcases the outcome of the electrochemical reactions involving the cathode and anode. Hydrogen and oxygen gas evolution is a tangible result of the electrolysis process occurring within the electrochemical device 100. The electrochemical device 100 can operate as an electrolyzer with the aid of various sensors, electrodes, and a selectively permeable membrane. The electrochemical reactions taking place within the electrolytic solution 110 can result in the generation of hydrogen and oxygen bubbles, as visually represented in FIG. 4A.

Figure 4B:
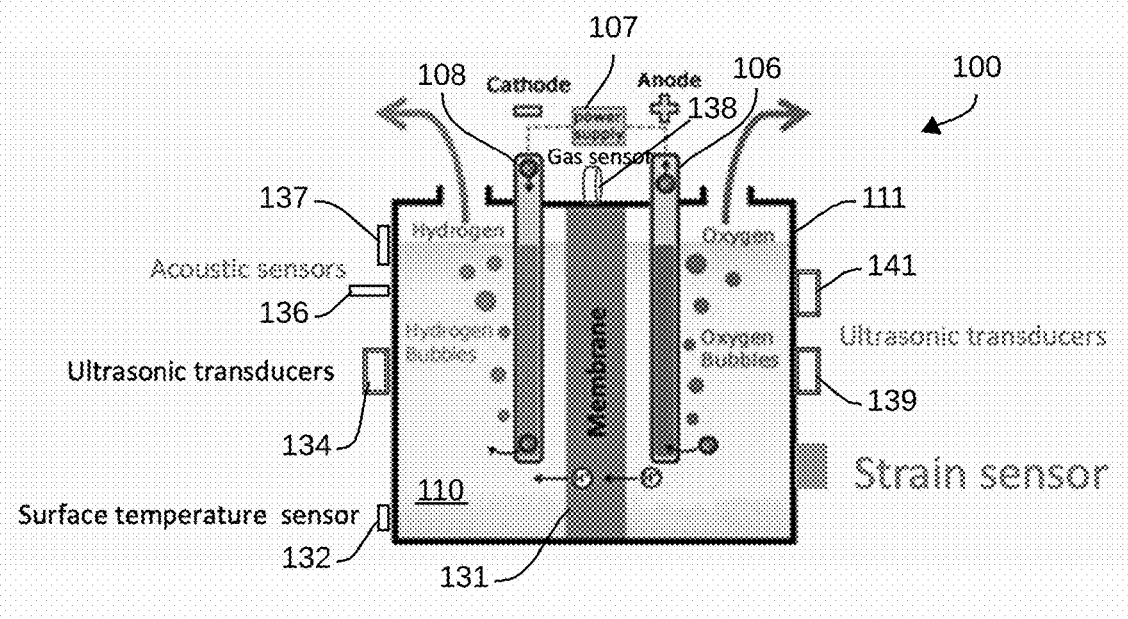
FIG. 4B illustrates a schematic diagram of a non-invasive real-time sensing array system on the electrochemical device, in accordance with another embodiment.

FIG. 4B illustrates a schematic diagram of the non-invasive real-time sensing system 100, in accordance with another embodiment. The embodiment shown in FIG. 4B is similar to the embodiment depicted in FIG. 4A, but with a different arrangement of sensors. For example, ultrasonic transducers 139 and 141 are shown with respect to the right side of the container 111 and ultrasonic transducer 134 is shown with respect to the left side of the container 111. One or more wideband acoustic sensors 136 and 137 are shown with respect to the upper left side of the container 111, which may be implemented as one or more two types of sensors (i.e., free-field and pressure field), which may be combined to sense wanted signals while eliminating extraneous interferences and noise.

Figures 5A, 5B:
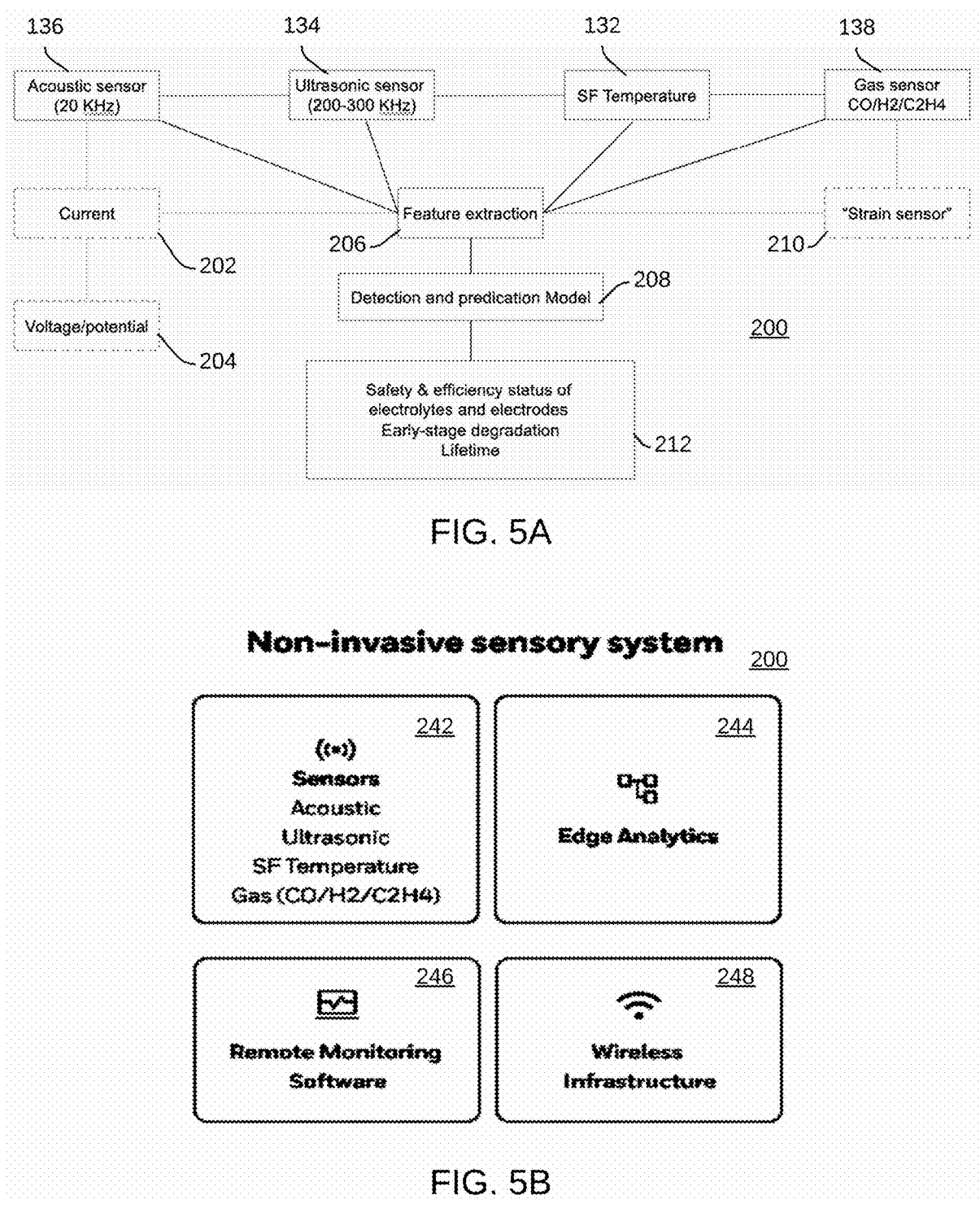
FIG. 5A illustrates a block diagram of a sensor system for analytics sensing and detection and data fusion in accordance with an embodiment.
FIG. 5B illustrates a block diagram of a sensor system for analytics sensing and detection in accordance with another embodiment.

FIG. 5A illustrates a block diagram of a sensor system 200 for analytical sensing and detection and data fusion in accordance with an embodiment. As shown in FIG. 5A, the sensing system 200 can include the acoustic sensor 136, which is subject to the current 202 and voltage/potential 204 shown in FIG. 5A. The acoustic sensor 136 can communicate with the ultrasonic sensor 134. The sensing system 200 can further include the temperature sensor 132, which can communicate with the ultrasonic sensor 134, and optionally with the gas sensor 138 to fuse the multi-sensor data based on the extracted feature space.

Data output from the acoustic sensor 136, the ultrasonic sensor 134, the temperature sensor 132 and the gas sensor 138 can be output and subject to signal feature extraction operations by a feature extraction module 206. Output from the feature extraction module 206 can be output of data fusion and input to a detection and prediction model 208. Data output from the detection and prediction model 208 can be input to an electrical-chemical-thermodynamic model 212, which uses the data output from the detection and prediction model 208 to generate data indicative of the safety and status of electrolytes and electrodes including early-stage degradation and lifetime data thereof.

The ultrasonic sensor 134 may be, for example, a piezoelectric transducer sensor (e.g., can be 100-1000 KHz, typical 200-800 KHz) being on the previously DUT to transmit pulse- and/or frequency modulated ultrasonic signals through electrolytes (electrolytic media), the signal capturing the property of such media which can be used to construct chemical-physical-thermal metrics during an operating cycle. The information can be used to, for example, determine the health situation and status of the charge and discharge cycles of electrolytes, along with the situation of electrode swelling which can lead to gas formation and chemo-mechanical effects such as low-efficiency, volume expansion, which are not only a safety and reliability problem, but also an issue of accelerated ageing.

The acoustic sensor 136 can be implemented in some embodiments as, for example, a MEMS SMD acoustic microphone with directivity towards inside of electrochemical device 100 and with a flexible and special filtration (from infrasound region 0.1 Hz with bandwidth at least 20 KHz) feature for measuring the electrode fracture of structure, and for measuring phase transitions during operation of the electrochemical device 100 or DUT. These phenomena frequently and/or periodically can result in emitting signal in a wide spectrum that can be processed by signal processing to extract the electrodes' signature or fingerprint attributed to electrochemical reaction grinding, gassing, and expansion and contraction. In some embodiments, the acoustic sensor 136 can be implemented as a MEMS or non-MEMS wideband free-field based sensor.

The SF temperature sensor 132 can be implemented as a surface temperature sensor that can track temperature and temperature change in correlation with the acoustic sensor 136 and the ultrasonic sensor 134 to construct the thermodynamic model 212 for safety and efficiency prediction. In addition, for the sake of modeling and data analytics verification in early adoption, it may be useful to select the gas sensor 138 to track the gas evolution with respect to electrolyte decomposition, for example, VOC's (volatile organic compounds), H2 (hydrogen), CO2 (carbon dioxide), CO (carbon monoxide), and or C2H4 (ethylene) can be possible gases released as a direct result of the electrochemical reaction of electrolyte decomposition in some reduction-oxidation processes. A strain sensor 210 can additionally be used as a part of the sensing system 200 and can communicate with the gas sensor 138 and the feature extraction module 206 to verify the expansion and contraction situation. A strain sensor can be piezoelectrical-based to sense pressure waves on the device wall. The piezo-electric based strain sensor can be in the form of an accelerometer or other types of sensing devices sensitive to pressure and structural changes.

The information gathered by various sensors, namely the acoustic sensor 136, ultrasonic sensor 134, temperature sensor 132, and gas sensor 138, can undergo processing through a feature extraction module 206. This module is responsible for extracting meaningful features from the collected data. The output generated by the feature extraction module 206 is then fed into a detection and prediction model represented by 208. This model analyzes the extracted features to make predictions and detections based on the input data.

The results from the detection and prediction model 208 are further utilized in a electrochemical and physical and thermodynamic models denoted as 212. The resultant models can leverage the output from the detection and prediction model to generate data that provides insights into the safety and status of both electrolytes and electrodes. This includes assessing factors such as early-stage degradation and the overall lifespan of these inside components.

In essence, the process of system 200 can involve a seamless flow of data from the sensors to the feature extraction module 206, followed by analysis through the data fusion, detection and prediction model, ultimately contributing to a comprehensive evaluation of the safety and condition of electrolytes and electrodes via the aforementioned electrochemical-thermodynamic model.

The feature extraction module 208 can function as a component responsible for analyzing the data collected from various sensors (acoustic sensor 136, ultrasonic sensor 134, temperature sensor 132, and gas sensor 138) and extracting meaningful features from that data and fuse them in the feature vector space. These features can be essential characteristics or patterns within the information that carry relevant insights or indications about the monitored electrochemical system.

After processing the sensor data, the feature extraction module 206 can produce an output, which can include the identified and isolated features. This output can be then input into the detection and prediction model 208. A role of this model is to analyze the extracted features, enabling it to make predictions and detections based on the patterns and information identified in the input data. The feature extraction module 206 essentially acts as a preprocessing and multi-sensor data fusion step, enhancing the efficiency of the subsequent detection and prediction model by distilling the most relevant information from the raw sensor data. This organized and refined input contributes to the accuracy of predictions and detections made by the overall system 200.

The embodiments involve integrating ultrasonic transducers, acoustic sensors, gas sensors, and temperature sensors to gain valuable insights into various phenomena. This innovative combination of sensors can be applied to emerging markets, including Original Equipment Manufacturers (OEMs) specializing in green hydrogen generation plants and lithium-ion battery (LIB), hydrogen fuel cell battery factories for electric vehicles. Additionally, the utility of the embodiments can extend to industries like petrochemicals and pharmaceuticals, where non-invasive monitoring of electrochemical processes offers distinct advantages over traditional methods.

The disclosed sensing system can include a sensor array of ultrasonic transducers and acoustic sensors, which can enable analytical detection of internal situations by penetrating through metallic wall sensing. This capability allows for the much early detection of deterioration or deformation in electrolyzers and electrolytes that are invisible externally. For instance, the sensing of gas evolution through ultrasonic means can identify issues before a cell dries up, thereby predicting electrode and/or electrolyte lifespan. This innovative approach is particularly beneficial for real-time inspection in the manufacturing processes of electric vehicle mega lithium-ion batteries and hydrogen generation plants.

As discussed above, the acoustic sensor 136 can be a MEMS (Micro-Electro-Mechanical System) SMD (Surface Mount Device) acoustic microphone, which is a type of microphone that can utilize MEMS technology and can be designed for surface mount applications. MEMS microphones are a type of miniature microphone that can integrate mechanical elements, such as diaphragms, with electronic components on a single chip. Note that MEMS technology involves the fabrication of miniature mechanical and electromechanical elements using techniques from microfabrication. In the context of a microphone, this typically includes a tiny diaphragm that responds to sound waves. In addition, Surface Mound Device (SMD) relates to a type of electronic component that can be designed to be mounted directly onto the surface of a printed circuit board (PCB). SMD components are compact and suitable for automated assembly processes.

Note that an acoustic microphone can convert sound waves into electrical signals. In a MEMS SMD acoustic microphone, this can be achieved through the interaction of the sound waves with the MEMS diaphragm, causing it to vibrate. The mechanical movement can be then converted into an electrical signal through the integrated electronics on the chip. In some embodiments, a pressure field sensing cell and sensing microphone may be used to purposely listen internally to the electrochemical device. In some embodiments, a pressure microphone may be used to measure the actual sound pressure on the surface of the microphone's diaphragm in a closed coupler on the electrochemical device's wall. The two types of acoustic sensors can work together to eliminate the background noise and extraneous disturbances to determine the correct signals emanating from within the electrochemical systems/devices or DUT.

FIG. 5B illustrates a block diagram of the sensor system 200 in accordance with another embodiment. The sensor system 200 can be utilized for analytics sensing and detection. The sensor system 200 shown in FIG. 5B is an alternative version of the sensor system 100 depicted in FIGS. 1A-1B and can function as a non-invasive sensory system. The sensor system 200 includes a group of sensors 242 (e.g., a sensor array) such as, for example, acoustic sensors, ultrasonic sensors, a temperature sensor, a gas sensor, and so on. The sensor system 200 can further include remote monitoring software 246, edge analytics 244, and wireless infrastructure 248. The group of sensors 242 can be implemented in the context of a non-intrusive sensor array such as the previously discussed sensor array 120.

The non-invasive sensory system 200 shown in FIG. 5B can be implemented to monitor and diagnose the inside of an electrolyzer (e.g., such as electrochemical device 100) for safety and efficiency. This diagnosis can be accomplished through insights into electrochemical reaction, electrolyte aging, status of charge, dried, wetted and gas-containing electrodes, along with other features such as electrode swelling and fracturing. Other features that can be detected and diagnosed include metal dissolution and electrolyte decomposition, and the shuttling of redox contaminants and unexpected increases in the electrolyte interphase.

Note that 'edge analytics' as referred to by edge analytics 244 can relate to a process of analyzing data on or near the edge of a network where the data is generated, rather than sending it to a centralized data-processing warehouse. In the context of a non-invasive sensor system that includes various sensors such as the aforementioned acoustic sensors, ultrasonic sensors, SF temperature sensor, gas sensor, and strain sensor, edge analytics can play a crucial role in performing real-time analysis and decision-making at the source of data generation, i.e., the edge of the network.

Edge analytics 244 can allow for the real-time processing of data collected by the sensors. Instead of sending all the raw data to a central server for analysis, the processing occurs locally on the device or at the edge of the network. This reduces latency and enables quicker responses to events. In addition, since only relevant and processed information is sent to the central system, edge analytics 244 can minimize the amount of data that may need to be transferred over the network. This may be particularly important when dealing with large volumes of sensor data, as it helps in optimizing bandwidth usage.

The analytics performed at the edge can enable local decision-making based on the sensor data. For example, in a non-invasive sensor system, the analytics could detect anomalies or patterns in acoustic, ultrasonic, temperature, gas, and strain data, allowing the system to respond immediately to potential issues or changes in the environment. Edge analytics 244 can also contribute to enhanced privacy by processing sensitive data locally, without transmitting it to external servers. This is important in scenarios where data security and privacy are critical, such as in sensor systems that monitor private or secure environments.

Edge analytics 244 can further improve scalability and efficiency in sensor networks by distributing the computational load. Instead of relying solely on a centralized server, each edge device can perform its own analytics, contributing to a more scalable and efficient system. In the context of a non-invasive sensor system with diverse sensors, edge analytics 244 can enable real-time processing, local decision-making, reduced data transfer, enhanced privacy, and scalability, contributing to a more responsive and efficient sensor network.

Figure 6:
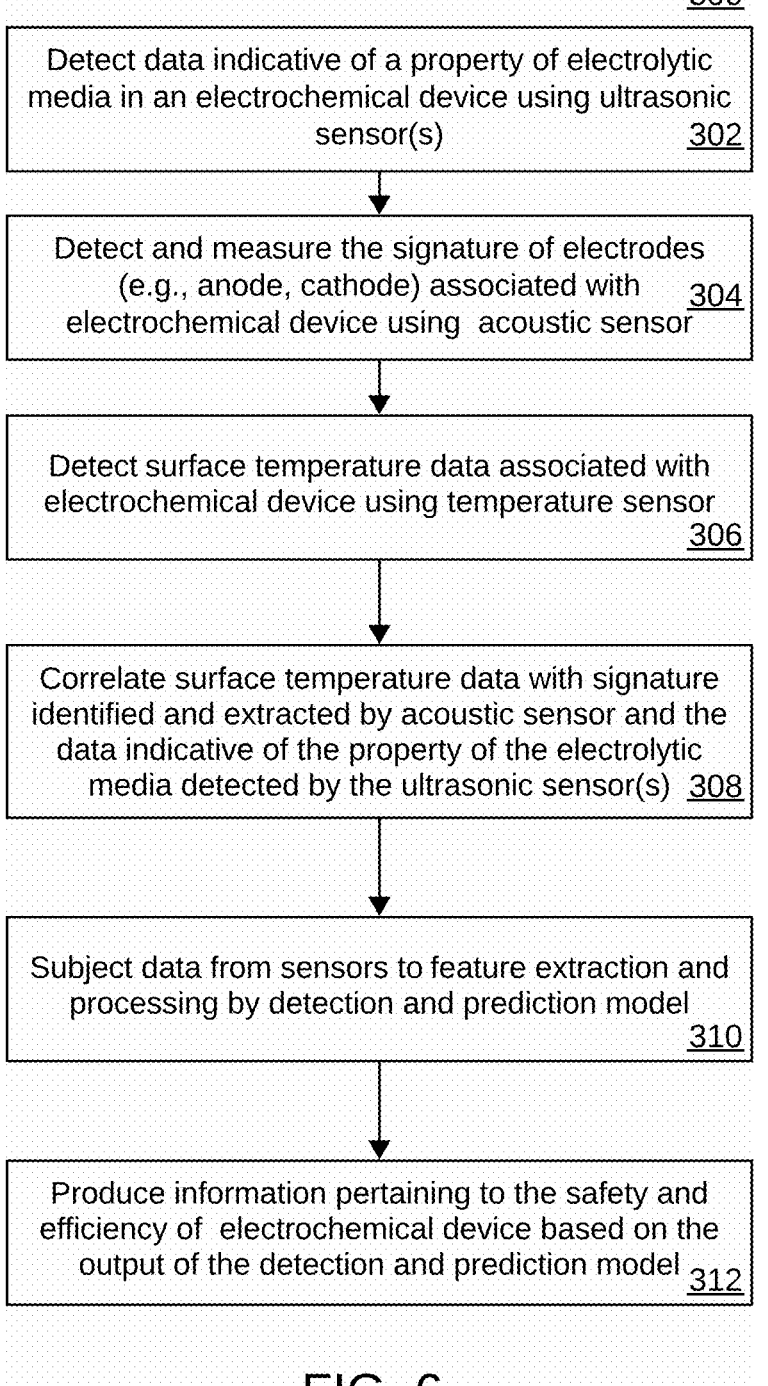
FIG. 6 illustrates a flow chart of operations depicting logical operational steps of a method for real-time monitoring an electrochemical device, in accordance with an embodiment.

FIG. 6 illustrates a flow chart of operations depicting logical operational steps of method 300 for monitoring an electrochemical device, in accordance with an embodiment. As indicated at block 302, a step or operation can be implemented for detecting data indicative of a property of electrolytic media in an electrochemical device using the ultrasonic sensors 134, 139. As shown at block 304, a step or operation can be implemented for detecting and measuring the signature of one or more electrodes (e.g., anode, cathode) associated with the electrochemical device 100 using the acoustic sensors 136. Next, as shown at block 306, a step or operation can be implemented for detecting surface temperature data associated with the electrochemical device 100 using the temperature sensor 132.

Then, as shown at block 308, a step or operation can be implemented for correlating the surface temperature data with the signature identified and extracted by the acoustic sensor and the data indicative of the property of the electrolytic media detected by the ultrasonic sensor. Then, as shown at block 310, a step or operation can be implemented for subjecting the data detected by the ultrasonic sensors 134, 139, the signature detected by the acoustic sensor 136, and the surface temperature data identified by the temperature sensor 132 to feature extraction and processing by the detection and prediction model 208. A step or operation can be the implemented as shown at block 312 to produce information pertaining to the safety and efficiency of the electrochemical device 100 based on the output of the detection and prediction model.

FIG. 7 illustrates additional and optional operational steps of the method 300 for monitoring an electrochemical device, in accordance with an embodiment. These steps involve the use of the gas sensor 138. A shown at block 316, a step or operation can be implemented for detecting and tracking a gas evolution and possible escape with respect to electrolyte decomposition of the electrolytic media of the electrochemical device using the gas sensor 138 to verify and correlate to the signal characteristics of acoustics and ultrasounds. As shown at block 318, a step or operation can be implemented to subject data output from the gas sensor 138 to feature extraction, data fusion and cross-correlation with data output from the ultrasonic sensors 138, 139, the acoustic sensor 136, and the temperature sensor 132. Then, as shown at block 320, a step or operation can be implemented for producing information pertaining to the safety and efficiency of electrolytic media and the electrode(s) of the electrochemical device 100 based at least in part on the correlated data.

Figure 8:
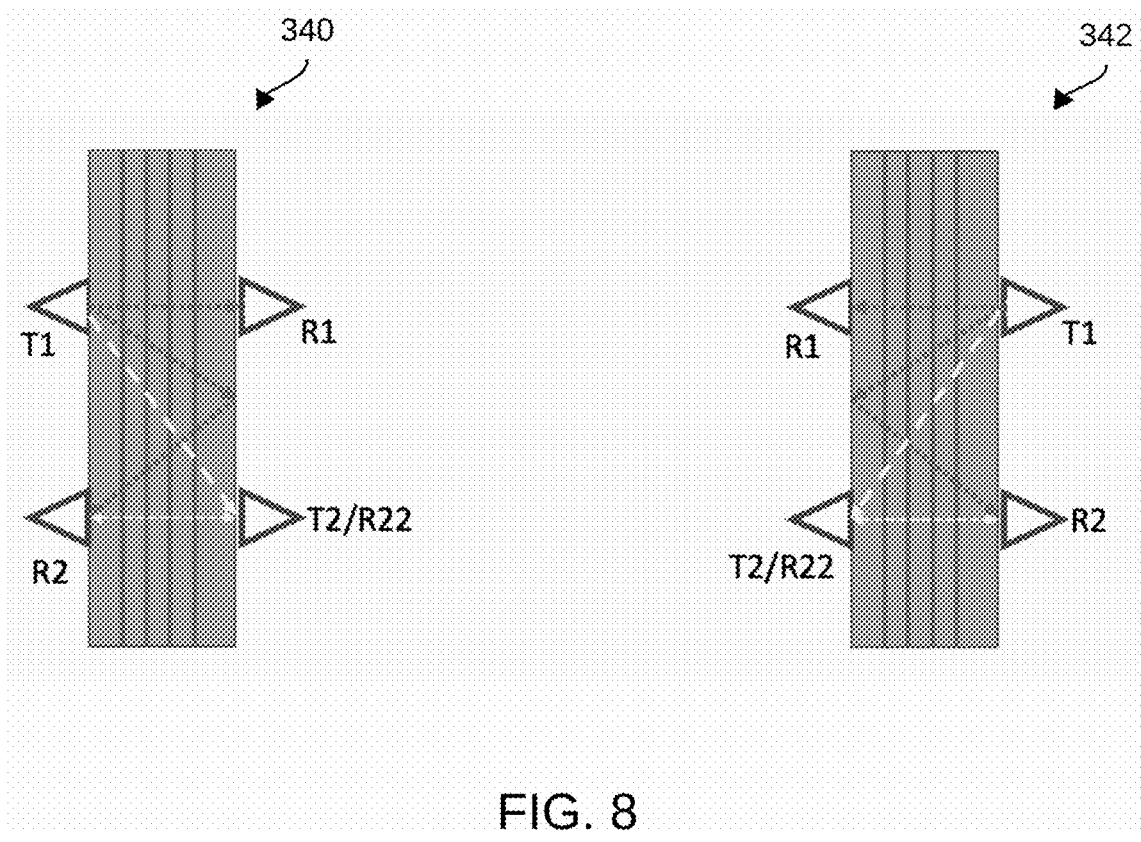
FIG. 8 illustrates schematic diagrams of multi-static ultrasonic sensing configurations, which can be implemented in accordance with an embodiment.

FIG. 8 illustrates schematic diagrams of multi-static ultrasonics 340 and 342, in accordance with an embodiment. In the multi-static ultrasonics 340 and 342, the exchange between ultrasonic transmitter (T) and receiver (R) can be facilitated through multiplexer control in software (SW) and firmware (FW). The multi-static ultrasonics 340 and 342 can be implemented as part of a non-intrusive sensing system for monitoring an electrochemical device such as the previously discussed electrochemical device 100.

The multi-static ultrasonics 340 and/or 342 can be used for detecting data indicative of a property of electrolytic media in the electrochemical device 100. In the operation of multi-static ultrasonics 340, the transmitter T1 can transmit a specific pulse and frequency modulated ultrasonics, while multiple receivers R1, R2, and R22 are open to intercept the ultrasonic waves as indicated by the dashed arrows depicted in the FIG. 8. Vice versa, in the operation of multi-static ultrasonics 342, the receiver R1 of multi-static ultrasonics 340 becomes the transmitter T1 that transmits a specific pulse and frequency modulated ultrasonics, wherein R1 which was multi-static ultrasonics T1 in 340, R2 (which was T2 in multi-static ultrasonics 340), R22 (which was R22 in multi-static ultrasonics 340) are open to intercept the ultrasonic waves of backward or forward scatterings. In addition, as discussed previously, other types of sensors may be implemented as a part of the disclosed non-intrusive sensing system.

For example, an acoustic sensor for detecting and measuring a signature of at least one electrode associated with a health condition of the electrochemical device can be implemented, along with a temperature sensor for detecting surface temperature data associated with the electrochemical data and correlating the surface temperature data with the signature identified and extracted by the acoustic sensor and the data indicative of the property of the electrolytic media detected by the multi-static ultrasonic sensors, wherein the data detected by the multi-static ultrasonic sensors, the signature detected by the acoustic sensor, and the surface temperature data identified by the temperature sensor can be subject to feature extraction and processing by a detection and prediction model to produce information pertaining to safety and operating efficiency of the electrochemical device.

Figure 9:
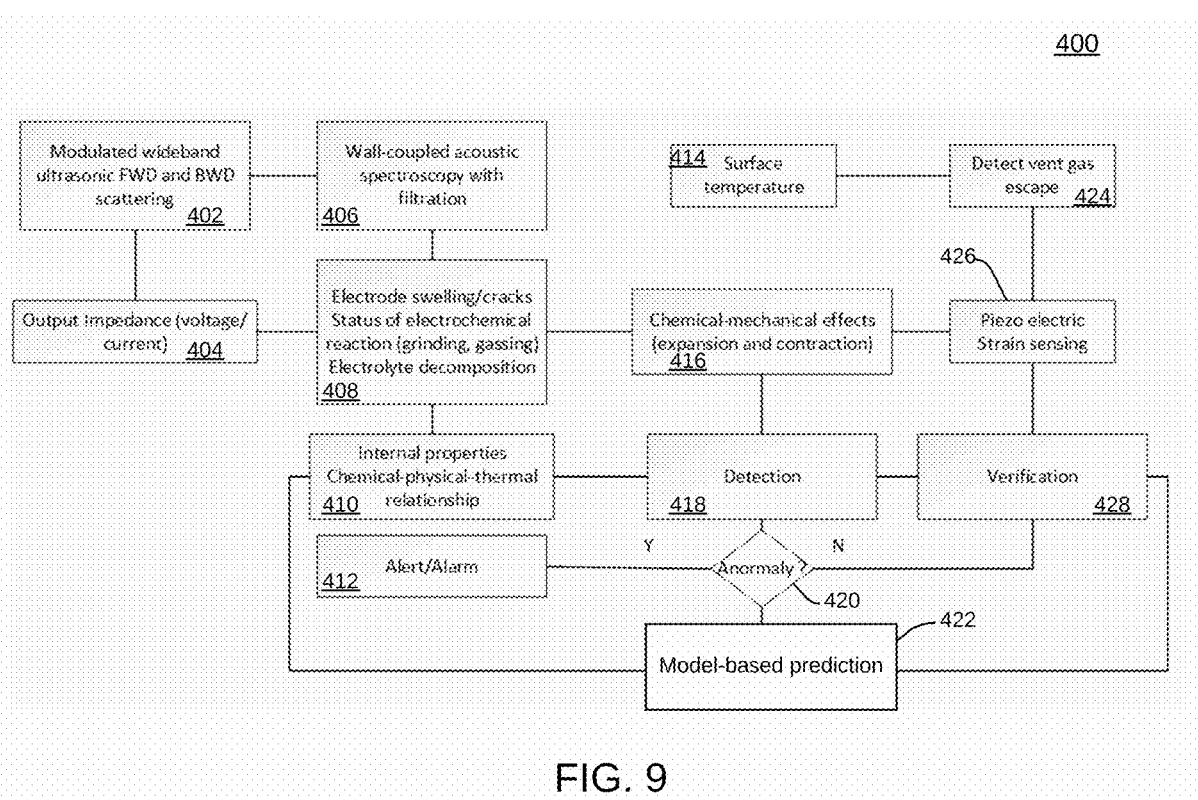
FIG. 9 illustrates a method for detection and prediction, which can be implemented in accordance with an embodiment.

FIG. 9 illustrates a method 400 for detection and prediction, which can be implemented in accordance with an embodiment. As shown at block 402, a step or operation can be implemented involving modulated wideband ultrasonic forward (FWD) and backward (BWD) scattering. Output from the aforementioned modulated wideband ultrasonic FWD and BWD scattering can be output impedance (voltage/current) as shown at block 404. As indicated at block 406, a step or operation can be implemented involving wall-coupled acoustic spectroscopy filtration.

As indicated at block 408, data can be generated regarding the status of an electrochemical reaction (e.g., grinding, gassing, etc.), along with electrode swelling/cracks, and electrolyte decomposition. This data can be used to develop the internal properties of the electrochemical device including chemical-physical-thermal relationships. This data can be used as part of a detection operation, as shown at block 418. The detection operation can also use information such as chemical-mechanical effects (expansion and contraction) as shown at block 416.

Other operations shown in FIG. 9 include a step or operation involving the detection of escaping vent gas, as shown at block 424, which includes data derived from surface temperature detection, as depicted at block 414. In addition to the detection operation shown at block 424, an operation involving piezo electric strain sensing as indicated at block 426. The information obtained from the operations depicted at blocks 414, 424, and 426 can be used for a verification operation, as shown at block 428.

An anomaly detection operation can be implemented as shown at decision block 420. Depending on the results of the operation depicted at decision block 420, an alert/alarm can be implemented, as shown at block 412. Finally, following implementation of the operation shown at decision block 420, a model-based prediction operation can be implemented, as shown at block 422.

It should be appreciated that although the operations of the devices, systems and/or method(s) herein are shown and described in a particular order, the order of the operations may be altered so that certain operations may be performed in an inverse order or so that certain operations may be performed, at least in part, concurrently with other operations. In another embodiment, instructions or sub-operations of distinct operations may be implemented in an intermittent and/or alternating manner.

At least some of the steps or operations described or features herein can be implemented using software instructions stored on a computer useable storage medium for execution by a computer. As an example, an embodiment of a computer program product includes a computer useable storage medium to store a computer readable program.

The computer-useable or computer-readable storage medium can be an electronic, magnetic, optical, electromagnetic, infrared, or semiconductor system (or apparatus or device). Examples of non-transitory computer-useable and computer-readable storage media include a semiconductor or solid-state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), a digital video disk (DVD), Flash memory, and so on.

Alternatively, embodiments may be implemented in hardware or in an implementation containing hardware and software elements. In embodiments that do utilize software, the software may include firmware, resident software, microcode, etc.

In some alternative implementations, the functions noted in the blocks may occur out of the order noted in the figures. For example, two blocks shown in succession may, in fact, be executed concurrently, or the blocks may sometimes be executed in the reverse order, depending upon the functionality involved. It will also be noted that the blocks of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Based on the foregoing, it can be appreciated that a number of different embodiments including preferred and alternative embodiments, are disclosed herein. For example, in an embodiment a non-intrusive sensing system for monitoring an electrochemical device, can be implemented, which can include multi-static ultrasonic sensors for detecting data indicative of a property of electrolytic media in an electrochemical device, an acoustic sensor for detecting and measuring a signature of at least one electrode associated with a health condition of the electrochemical device, and a temperature sensor for detecting surface temperature data associated with the electrochemical data and correlating the surface temperature data with the signature identified and extracted by the acoustic sensor and the data indicative of the property of the electrolytic media detected by the multi-static ultrasonic sensors.

In an embodiment of the non-intrusive sensing system, the data detected by the multi-static ultrasonic sensors, the signature detected by the acoustic sensor, and the surface temperature data identified by the temperature sensor can be subject to feature extraction and processing by a detection and prediction model to produce information pertaining to safety and operating efficiency of the electrochemical device.

In an embodiment of the non-intrusive sensing system, the sensor data derived from the multi-static ultrasonic sensors, the acoustic sensor, and the temperature sensor can be fused based on multiple sensor inputs from the multi-static ultrasonic sensors and the acoustic sensor to form a uniform feature vector space for faulty detection and iden-tification and prediction.

In an embodiment of the non-intrusive sensing system, the health condition of the electrochemical device may include data or information related to, for example, fracture or cracks of electrodes.

In an embodiment of the non-intrusive sensing system, a multi-species gas sensor for detecting and tracking an out-come of a gas evolution and potential venting with respect to electrolyte decomposition of the electrolytic media of the electrochemical device, wherein data output from the multi-species gas sensor, can be subject to the feature extraction and correlation with data output from the ultrasonic sensor, the acoustic sensor and temperature sensor for use in pro-ducing the information pertaining to the safety and the efficiency of the electrolytic media and the at least one electrode of the electrochemical device.

In an embodiment of the non-intrusive sensing system, the electrochemical device may be a device under test (DUT).

In an embodiment of the non-intrusive sensing system, the ultrasonic sensor can be located on the electrochemical device and transmits a pulse and/or frequency-modulated ultrasonic signals penetrating through the electrolytic media, the pulse and/or frequency-modulated ultrasonic signals comprising data indicative of a property of the electrolytic media, wherein the property of the electrolytic media is usable for a construction of chemical-physical thermal met-rics during a cycle, and the data is determinative of one or more of: the health status of reduction-oxidation or charge and discharge cycles of the electrochemical device.

In an embodiment of the non-intrusive sensing system, the acoustic sensor can be a wideband acoustic sensor with at least 20 KHz bandwidth, wherein the wideband acoustic sensor can be located on the electrochemical device and the signature of the at least one electrode associated with the electrochemical device can allow the acoustic sensor to measure an electrode fracture and phase transitions of the at least one electrode during an operation of the electrochemi-cal device.

In an embodiment of the non-intrusive sensing system, the acoustic sensor may be, for example, a MEMS or non-MEMS wideband free-field sensor and pressure-field sensor elements or microphones in which the microphones form a part of a wall and measures sound pressure on the wall of a device under test (DUT).

In an embodiment of the non-intrusive sensing system, the microphones can measure the sound pressure where a sensor front-end is located.

In an embodiment of the non-intrusive sensing system, the acoustic sensor can include two or more types of acoustic sensors that can work together to eliminate background noise and extraneous disturbances to determine correct signals emanating from within the electrochemical device.

In an embodiment of the non-intrusive sensing system, the temperature sensor can be implemented as a surface temperature sensor that can track a temperature and a temperature change in correlation with acoustic and ultrasonic sensory data respectively output from the acoustic sensor and the ultrasonic sensor, which together can facili-tate development of an internal thermodynamic model with respect to the electrochemical device for safety and effi-ciency prediction.

In an embodiment of the non-intrusive sensing system, a piezoelectric strain sensor can verify expansion and con-traction data and can correlate the expansion and contraction data with ultrasonic signal signatures derived from the multi-static ultrasonic sensors.

In an embodiment of the non-intrusive sensing system, the piezoelectric strain sensor can detect pressure waves in a wall of the electrochemical device.

In an embodiment of the non-intrusive sensing system, the piezoelectric strain sensor may include one or more: an accelerometer or another sensing device that is sensitive to surface pressure and structural variation.

In an embodiment of the non-intrusive sensing system, the acoustic sensor can include a signal processor that can extract the signature of the at least one electrode attributed to one or more of, for example: electrochemical reaction grinding, gassing, and expansion and contraction.

In another embodiment, a non-intrusive sensing system for monitoring an electrochemical device, can include: a plurality of ultrasonic sensors for detecting data indicative of a property of electrolytic media in an electrochemical device; an acoustic sensor for detecting and measuring a signature of at least one electrode associated with a health condition of the electrochemical device; a strain sensor that can be configured to verify expansion and contraction data and correlate the expansion and contraction data with ultra-sonic signal signatures derived from the plurality of ultra-sonic sensors, wherein the strain sensor can be further configured to detect pressure within a wall of the electro-chemical device; and a temperature sensor for detecting surface temperature data associated with the electrochemical data and correlating the surface temperature data with the signature identified and extracted by the acoustic sensor and the data indicative of the property of the electrolytic media detected by the plurality of ultrasonic sensors.

In an embodiment, the data detected by the plurality of ultrasonic sensors, the signature detected by the acoustic sensor, and the surface temperature data identified by the temperature sensor can be subject to feature extraction and processing by a detection and prediction model to produce information pertaining to safety and operating efficiency of the electrochemical device.

In still another embodiment, a method of operating a non-intrusive sensing system that monitors an electrochemi-cal device, can involve: detecting with multi-static ultra-sonic sensors, data indicative of a property of electrolytic media in an electrochemical device using multi-static ultra-sonic sensors configured for detecting the data indicative of the property of the electrolytic media in the electrochemical device; detecting and measuring with an acoustic sensor, a signature of at least one electrode associated with a health condition of the electrochemical device; detecting with a temperature sensor, surface temperature data associated with the electrochemical data and correlating the surface tem-perature data with the signature identified and extracted by the acoustic sensor and the data indicative of the property of the electrolytic media detected by the multi-static ultrasonic sensors; and subjecting the data detected by the multi-static ultrasonic sensors, the signature detected by the acoustic sensor, and the surface temperature data identified by the temperature sensor to feature extraction and processing by a detection and prediction model for the generation of information pertaining to safety and operating efficiency of the electrochemical device.

An embodiment of the method can further involve fusing sensor data derived from the multi-static ultrasonic sensors, the acoustic sensor, and the temperature sensor based on multiple sensor inputs from the multi-static ultrasonic sensors and the acoustic sensor to form a uniform feature vector space for faulty detection and identification and prediction.

An embodiment of the method can further involve verifying with a strain sensor expansion and contraction data and correlating the expansion and contraction data with ultrasonic signal signatures derived from the multi-static ultrasonic sensors.

In an embodiment of the method, the strain sensor can pressure within a wall of the electrochemical device.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A non-intrusive sensing system for monitoring an electrochemical device, comprising:

multi-static ultrasonic sensors for detecting data indicative of a property of electrolytic media in an electrochemical device;

an acoustic sensor for detecting and measuring a signature of at least one electrode associated with a health condition of the electrochemical device; and a temperature sensor for detecting surface temperature data associated with the electrochemical data and correlating the surface temperature data with the signature identified and extracted by the acoustic sensor and the data indicative of the property of the electrolytic media detected by the multi-static ultrasonic sensors, wherein the data detected by the multi-static ultrasonic sensors, the signature detected by the acoustic sensor, and the surface temperature data identified by the temperature sensor are subject to feature extraction and processing by a detection and prediction model to produce information pertaining to safety and operating efficiency of the electrochemical device.

2. The non-intrusive sensing system of claim 1 wherein sensor data derived from the multi-static ultrasonic sensors, the acoustic sensor, and the temperature sensor are fused based on multiple sensor inputs from the multi-static ultrasonic sensors and the acoustic sensor to form a uniform feature vector space for faulty detection and identification and prediction.

3. The non-intrusive sensing system of claim 1 wherein the health condition of the electrochemical device comprises a fracture or cracks of electrodes.

4. The non-intrusive sensing system of claim 1 further comprising a multi-species gas sensor for detecting and tracking an outcome of a gas evolution and potential venting with respect to electrolyte decomposition of the electrolytic media of the electrochemical device, wherein data output from the multi-species gas sensor is subject to the feature extraction and correlation with data output from the ultrasonic sensor, the acoustic sensor and temperature sensor for use in producing the information pertaining to the safety and the efficiency of the electrolytic media and the at least one electrode of the electrochemical device.

5. The non-intrusive sensing system of claim 1 wherein the electrochemical device comprises a device under test (DUT).

6. The non-intrusive sensing system of claim 1 wherein the ultrasonic sensor is located on the electrochemical device and transmits a pulse and/or frequency-modulated ultrasonic signals penetrating through the electrolytic media, the pulse and/or frequency-modulated ultrasonic signals comprising data indicative of a property of the electrolytic media, wherein the property of the electrolytic media is usable for a construction of chemical-physical thermal metrics during a cycle, and the data is determinative of at least one of: a health status of reduction-oxidation or charge and discharge cycles of the electrochemical device.

7. The non-intrusive sensing system of claim 1 wherein the acoustic sensor comprises a wideband acoustic sensor with at least 20 KHz bandwidth, wherein the wideband acoustic sensor is located on the electrochemical device and the signature of the at least one electrode associated with the electrochemical device allows the acoustic sensor to measure an electrode fracture and phase transitions of the at least one electrode during an operation of the electrochemical device.

8. The non-intrusive sensing system of claim 7 wherein the acoustic sensor comprises a MEMS or non-MEMS wideband free-field sensor and/or pressure-field sensor elements or microphones in which the microphones form a part of a wall and measures sound pressure on the wall of a device under test (DUT).

9. The non-intrusive sensing system of claim 8 wherein the microphones measure the sound pressure where a sensor front-end is located.

10. The non-intrusive sensing system of claim 1 wherein the acoustic sensor comprises at least two types of acoustic sensors that work together to eliminate background noise and extraneous disturbances to determine correct signals emanating from within the electrochemical device.

11. The non-intrusive sensing system of claim 1 wherein the temperature sensor comprises a surface temperature sensor that tracks a temperature and a temperature change in correlation with acoustic and ultrasonic sensory data respectively output from the acoustic sensor and the ultrasonic sensor, which together facilitate development of an internal thermodynamic model with respect to the electrochemical device for safety and efficiency prediction.

12. The non-intrusive sensing system of claim 1 further comprising a piezoelectric strain sensor that verifies expansion and contraction data and correlates the expansion and contraction data with ultrasonic signal signatures derived from the multi-static ultrasonic sensors.

13. The non-intrusive sensor system of claim 12 wherein the piezoelectric strain sensor detects pressure waves in a wall of the electrochemical device.

14. The non-intrusive sensor system of claim 12 wherein the piezoelectric strain sensor comprises at least one of: an accelerometer or a sensing device sensitive to surface pressure and structural variation.

15. The non-intrusive sensing system of claim 1 wherein the acoustic sensor comprises a signal processor that extracts the signature of the at least one electrode attributed to at least one of: electrochemical reaction grinding, gassing, and expansion and contraction.

16. A non-intrusive sensing system for monitoring an electrochemical device, comprising:

a plurality of ultrasonic sensors for detecting data indicative of a property of electrolytic media in an electrochemical device;

an acoustic sensor for detecting and measuring a signature of at least one electrode associated with a health condition of the electrochemical device;

a strain sensor that verifies expansion and contraction data and correlates the expansion and contraction data with ultrasonic signal signatures derived from the plurality of ultrasonic sensors, wherein the strain sensor further detects pressure within a wall of the electrochemical device; and a temperature sensor for detecting surface temperature data associated with the electrochemical data and correlating the surface temperature data with the signature identified and extracted by the acoustic sensor and the data indicative of the property of the electrolytic media detected by the plurality of ultrasonic sensors, wherein the data detected by the plurality of ultrasonic sensors, the signature detected by the acoustic sensor, and the surface temperature data identified by the temperature sensor are subject to feature extraction and processing by a detection and prediction model to produce information pertaining to safety and operating efficiency of the electrochemical device.

17. A method of operating a non-intrusive sensing system that monitors an electrochemical device, comprising:

detecting with multi-static ultrasonic sensors, data indicative of a property of electrolytic media in an electrochemical device using multi-static ultrasonic sensors configured for detecting the data indicative of the property of the electrolytic media in the electrochemical device;

detecting and measuring with an acoustic sensor, a signature of at least one electrode associated with a health condition of the electrochemical device;

detecting with a temperature sensor, surface temperature data associated with the electrochemical data and correlating the surface temperature data with the signature identified and extracted by the acoustic sensor and the data indicative of the property of the electrolytic media detected by the multi-static ultrasonic sensors; and subjecting the data detected by the multi-static ultrasonic sensors, the signature detected by the acoustic sensor, and the surface temperature data identified by the temperature sensor to feature extraction and fusion and processing by a detection, classification, identification and prediction model for the generation of information pertaining to safety and operating efficiency of the electrochemical device.

18. The method of claim 17 further comprising fusing sensor data derived from the multi-static ultrasonic sensors, the acoustic sensor, and the temperature sensor based on multiple sensor inputs from the multi-static ultrasonic sensors and the acoustic sensor to form a uniform feature vector space for faulty detection, classification and identification and prediction.

19. The method of claim 17 further comprising:

verifying with a strain sensor expansion and contraction data; and correlating the expansion and contraction data with ultrasonic signal signatures derived from the multi-static ultrasonic sensors.

20. The method of claim 19 wherein the strain sensor detects pressure within a wall of the electrochemical device.

* * * * *